(12) United States Patent
Hafner (10) Patent No.: US 8,795,275 B2
(45) Date of Patent: *Aug. 5, 2014

(54) TUBULAR SHAFT INSTRUMENT

(75) Inventor: Dieter Hafner, Tübingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 588 days.

This patent is subject to a terminal disclaimer.

(21) Appl. No.: 12/444,336

(22) PCT Filed: Sep. 26, 2007

(86) PCT No.: PCT/EP2007/008389
§ 371 (c)(1),
(2), (4) Date: Apr. 3, 2009

(87) PCT Pub. No.: WO2008/040486
PCT Pub. Date: Apr. 10, 2008

(65) Prior Publication Data
US 2010/0016879 A1  Jan. 21, 2010

(30) Foreign Application Priority Data

Oct. 5, 2006  (DE) .................. 10 2006 046 919
Oct. 5, 2006  (DE) .................. 10 2006 046 920
Oct. 5, 2006  (DE) .................. 10 2006 047 204
Oct. 5, 2006  (DE) .................. 10 2006 047 215
Nov. 29, 2006  (DE) .................. 10 2006 056 405
Dec. 14, 2006  (DE) .................. 10 2006 059 175

(51) Int. Cl.
*A61B 18/18* (2006.01)
*A61B 17/32* (2006.01)

(52) U.S. Cl.
USPC ............................................. 606/51; 606/171

(58) Field of Classification Search
USPC ............ 606/190, 45, 171, 37, 29–31, 51–52, 606/167, 205–209
See application file for complete search history.

(56) References Cited

U.S. PATENT DOCUMENTS

| 5,293,863 | A |   | 3/1994 | Zhu et al. |
| 5,445,638 | A | * | 8/1995 | Rydell et al. ............... 606/51 |
| 5,556,407 | A | * | 9/1996 | Wurster et al. ............. 606/174 |
| 5,599,350 | A |   | 2/1997 | Schulze et al. |
| 5,611,798 | A |   | 3/1997 | Eggers |

(Continued)

FOREIGN PATENT DOCUMENTS

| CN | 101516285 A | 8/2009 |
| DE | 42 04 051   | 8/1993 |

(Continued)

OTHER PUBLICATIONS

International Search Report for PCT/EP2007/008389.

(Continued)

*Primary Examiner* — Nicholas Lucchesi
*Assistant Examiner* — Weng Lee
(74) *Attorney, Agent, or Firm* — Dickstein Shapiro LLP (57) ABSTRACT

The present application relates to a tubular shaft instrument for separating tissue. The invention relates to a tubular shaft instrument that results in a more reliable, cleaner separation of tissue. To achieve this, in contrast to conventional cutting devices, the blade is not displaced through the fixed tissue, but glides over the latter until a complete separation is ascertained.

28 Claims, 9 Drawing Sheets

(56) References Cited

U.S. PATENT DOCUMENTS

| | | | |
|---|---|---|---|
| 5,797,938 A * | 8/1998 | Paraschac et al. | 606/167 |
| 6,500,176 B1 * | 12/2002 | Truckai et al. | 606/51 |
| 6,626,901 B1 * | 9/2003 | Treat et al. | 606/29 |
| 6,679,882 B1 | 1/2004 | Kornerup et al. | |
| 2002/0188294 A1 | 12/2002 | Couture et al. | |
| 2003/0199870 A1 | 10/2003 | Truckai et al. | |
| 2009/0043305 A1 * | 2/2009 | Brodbeck et al. | 606/52 |
| 2010/0030213 A1 | 2/2010 | Hafner | |

FOREIGN PATENT DOCUMENTS

| | | |
|---|---|---|
| DE | 44 21 822 | 10/1995 |
| DE | 44 44 166 | 6/1996 |
| DE | 100 31 773 | 11/2001 |
| DE | 10 2004 040 959 | 4/2006 |
| EP | 0717960 | 6/1996 |
| JP | 9-122138 A | 5/1997 |
| JP | 11-47150 A | 2/1999 |
| WO | WO-2005-004735 | 1/2005 |

OTHER PUBLICATIONS

Written Opinion of the International Searching Authority for for PCT/EP2007/008389.

German Examination Report for DE 10 2006 047 204.7-65.

* cited by examiner

TUBULAR SHAFT INSTRUMENT

BACKGROUND OF THE INVENTION

The invention relates to a tubular shaft instrument.

In modern medicine, attempts are generally made to keep the damage to intact tissue to a minimum. Thus, when circumstances permit, minimally invasive surgery is usually the preferred method used to perform an operative intervention. Small incisions and little trauma to the tissue lead to a lower sensation of pain after the operation and to rapid recovery and mobilization of the patient. This also applies to laparoscopic surgery during which complex operations are performed in the abdominal cavity.

Operations of this type and the instruments required for them present a particular challenge to the manufacturers of medical instruments as the majority of the operative steps are performed in very restricted spaces and without direct visual contact. Thus the medical instruments used must not only be able to operate in the smallest spaces but must also function so reliably that visual monitoring is superfluous. The instruments are preferably constructed such that even without visual contact the operating surgeon always has feedback which enables him to draw conclusions about the progress of the operation.

This applies particularly to all instruments that are suitable for the separation of tissue. As scalpels having an open blade are, if anything, unsuitable for minimally invasive surgery (cf. DE 44 44 166 A1), scissors-type or tong-type instruments are frequently resorted to, which cover the blade during insertion of the instrument on one hand and simultaneously take on a holding function for the tissue to be cut on the other.

It has also proven advantageous in minimally invasive surgery to perform coagulation of the tissue prior to separation in order to prevent bleeding. It is known from prior art to provide instruments that have integrated coagulation and cutting devices. Here the tissue on a fixing plane is clamped and coagulated in a first step. In a second step, a knife having a blade, which is substantially perpendicular to the fixing plane and protrudes over the tissue on both sides, is guided through the tissue. This displacement is carried out substantially parallel to the fixing plane. This prior art emerges, for example, from U.S. 2003/0199870 A1, U.S. Pat. No. 6,679,882 B1, EP 717 960 B1, U.S. 2002/0188294 A1, WO 2005/004735 A1.

On the other hand, it is known from U.S. Pat. No. 6,626,901 B1 to roll a blade similar to a pizza cutter over the tissue, instead of the knife, and thus to perform the incision. Whilst the last-mentioned method is very intricate and makes particular demands on the design of the instrument, the other methods also have numerous drawbacks. In the last-mentioned method, the clamped tissue is essentially pushed out of the mouth part by the displacement of the knife and only part of the tissue held is separated. During separation, a high single-point load is exerted on the tissue which in turn means that there is no guarantee of a clean cut when the blade is worn. The tissue is crushed until it virtually tears. There is a danger that the cut edge will spread so far that it passes the coagulated region and the vessel seal already performed will tear open again. As the blade or cutter only rests on one point on the tissue, the cutter wears quickly.

BRIEF DESCRIPTION OF THE DRAWINGS

The invention will be described in the following based on embodiments which will be explained in greater detail by means of drawings.

The same reference numerals are used in the following description for identical parts and parts acting in an identical manner.

DETAILED DESCRIPTION OF THE INVENTION

An object of the present invention is to provide an easy to operate tubular shaft instrument for separating tissue, which guarantees reliable separation with minimum damage to the surrounding tissue.

This object is achieved in the case of a tubular shaft instrument, in particular an electrosurgical tubular shaft instrument, for separating tissue, comprising:
a tubular shaft,
a first and a second mouth part having clamping surfaces for fixing tissue in a fixing plane, whereby at least one of the mouth parts is joined to the tubular shaft, and
a cutting device having a blade that is for cutting of the fixed tissue and that is displaceable in a cutting direction by means of an actuating device,
wherein
the blade is displaceably guided substantially parallel to the fixing plane and is preloaded against the fixing plane during cutting by means of a preloading device.

An essential idea of the invention is thus not to displace the blade through the fixing plane and thus through the tissue but to guide said blade by means of a guide above or below the fixing plane, whereby the blade is pressed against the fixing plane by means of the preloading device. The blade thus glides with a defined contact pressure, preferably in back and forth movements, over the tissue and thus over the fixing plane until the tissue is completely separated. As a result, separation of the tissue and not tearing due to mechanical pressure is ascertained. The force of the preloading device acts substantially perpendicular to the fixing plane.

Preferably, the preloading device comprises a resilient guide wire having a curvature, said wire being substantially rigidly joined to the blade and being guided in the tubular shaft ii such a manner that the blade is preloaded in relation to the tubular shaft in the direction of the fixing plane. The said force, acting substantially perpendicular to the fixing plane, may thus be built up by means of a resilient actuating element in the form of a guide wire The force applied acts in relation to the tubular shaft in which the wire is guided. In the simplest case, the guide wire thus has a kink.

The resilient guide wire uses a section of the tubular shaft at least for the force reversal or support.

Preferably, the preloading device includes a crimp, which is disposed in the guide wire such that it is close to the distal end of the tubular shaft when the blade is pushed forward. Thus the crimp is able to transfer the force arising due to the blade pressing against the cutting plane to the tubular shaft. For the tubular shaft instrument's user, the guide wire serves merely to move the blade within the cutting device. In the best case, there are no rotational forces acting on the user as the tubular shaft absorbs the contact pressure. For a functional arrangement of the guide wire, it is necessary that the crimp and the curvature lie substantially in the cutting plane that stands perpendicular on the fixing plane. Naturally, the guide may also be replaced by a guide rail having the said resilient properties perpendicular to the fixing plane. In this case too, preloading may be generated by the shape of the rail.

Preferably, at least one of the two clamping portions comprises an opening extending along the direction of cutting, which forms a blade guide. The substantially oblong clamping portions may include side parts formed in pairs having a channel in which the cutting device is guided along the direction of cutting.

Preferably, the blade includes at least one section which runs substantially parallel to the fixing plane. Also conceivable is a cutting device having a plurality of blades, whereby a plurality of blade sections run parallel to the fixing plane.

Preferably, the blade is curved so as to be convex in sections at least. Thus the blade is designed such that during displacement of the blade in the direction of cutting, said blade glides over the tissue preloaded in the fixing plane. This is particularly advantageous if the tissue to be separated is so tough that it cannot be separated by means of one cut. The blade's profile acts in this case like a ramp which guides the blade into a position above the fixing plane. There the blade glides over the tissue until said tissue is completely separated. The preloading device provides the necessary contact pressure.

Preferably, the tubular shaft instrument comprises a ramp-shaped blade guide, which is designed and disposed such that, by moving in the direction of cutting, it brings the blade out of a starting position at a distance from the fixing plane onto the fixing plane. Preferably, the blade is thus supported in a starting position which is at a distance from the fixing plane and from the clamping surfaces of the mouth parts. Only when the tissue is fixed between the clamping surfaces is the blade brought to them by a displacement parallel to the fixing plane. When the blade is shielded in the starting position, the tissue can be picked up intact. If the tubular shaft instrument is an electrosurgical instrument having electrodes for coagulation of the tissue held, it is possible to prevent premature cutting of the tissue.

Preferably, the blade guide is designed such that the blade may be brought into a starting position close to the fulcrum of the mouth parts, in particular in the tubular shaft.

Preferably, the clamping surfaces have electrodes for supplying high-frequency ("HF") coagulation currents to the tissue held. Thus the tissue held may be cauterized prior to or during cutting by a high-frequency coagulation current, which guarantees reliable sealing of the blood vessels prior to or during the incision.

Preferably, the blade is microtoothed in sections at least.

Figure 1:
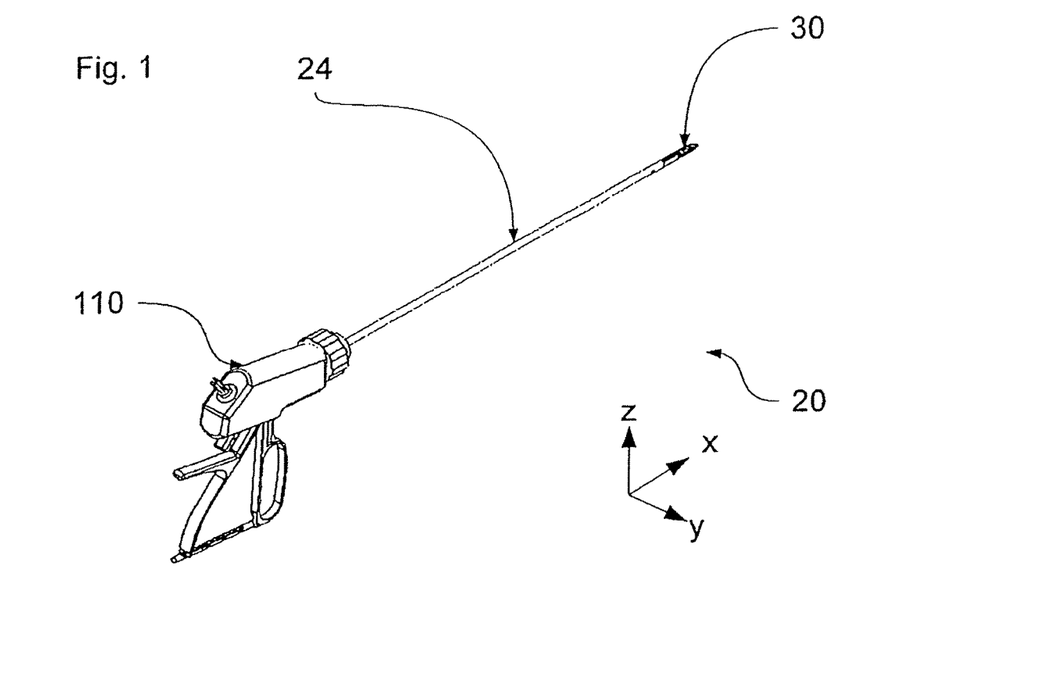
FIG. 1 illustrates a tubular shaft instrument for separating tissue according to a disclosed embodiment.

FIG. 1 provides a rough overview of an embodiment of a tubular shaft instrument 20 according to the invention. It shows three functional components of the tubular shaft instrument 20, a handle 110, a longish tubular shaft 24 and a tool head 30 disposed on the distal end of tube shaft 24. Tool head 30 provides the tubular shaft instrument's actual functionality. It is used for cutting and/or coagulating tissue. Handle 110 controls the movement of tool head 30. In particular, mouth parts 10, 10' (cf. FIG. 2) may be closed as well as opened by means of handle 110 for fixing, coagulating and cutting tissue.

Figure 2:
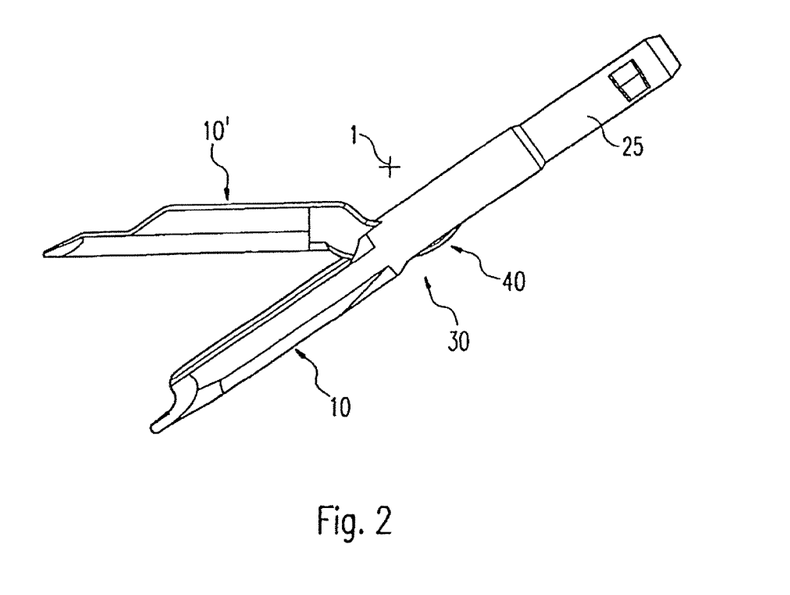
FIG. 2 illustrates the tool head of the tubular shaft instrument from FIG. 1, comprising a first and a second mouth part according to a disclosed embodiment.

FIG. 2 shows an embodiment of a tool head 30 according to the invention, comprising a first mouth part 10 and a second mouth part 10'. First mouth part 10 is an oblong body having on its side facing tubular shaft 24 an adapter 25, which is rigidly joined to said tubular shaft 24. Second mouth part 10' is attached to first mouth part 10 by way of an articulation 40 and may be brought from an open position for seizing the tissue into a closed position for fixing the tissue. Articulation 40 is designed such that a virtual fulcrum 1 or pivot is located outside first and second mouth parts 10, 10'. Unlike conventional articulations 40 for such instruments, fulcrum 1 is not, therefore, located in the region where mouth parts 10, 10' engage or in tubular shaft 24 close to the longitudinal axis of tube shaft 24. The mechanism of articulation 40 illustrated acts such that a virtual fulcrum 1 is created above the side of the tubular shaft instrument which faces second mouth part 10'.

Figure 9:
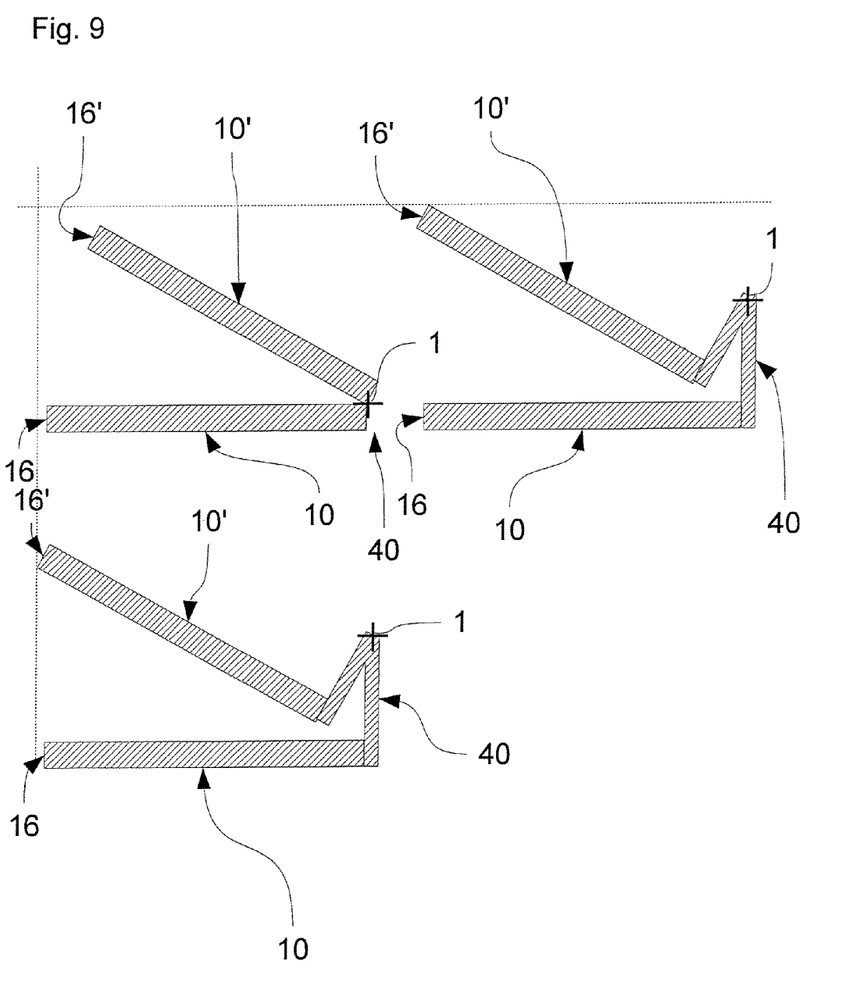
FIG. 9 illustrates a schematic diagram of two different articulations according to a disclosed embodiment.

The particular advantages of such a relocated fulcrum 1 are shown on the basis of the schematic diagrams of FIG. 9. Illustrated in the top left-hand corner is a conventional articulation, the fulcrum 1 of which is located substantially on the longitudinal axes of mouth parts 10 and 10'. In the open position, tip 16' of second mouth part 10' is offset backwards in relation to tip 16 of first mouth part 10. However, this is not the case with articulation 40 according to the invention, which is shown schematically in the other two diagrams of FIG. 9. Here fulcrum 1 is located noticeably above the longitudinal axes of both oblong mouth parts 10, 10'. With the same opening in respect of the angle formed by first mouth part 10 in relation to second mouth part 10', tip 16' of second mouth part 10' is located substantially on or in front of a perpendicular straight line through tip 16 of first mouth part 10 even in the open state. If second mouth part 10' is opened in relation to first mouth part 10, there is thus not only a rotary displacement during which the relative alignment of second mouth part 10' changes in relation to first mouth part 10 but there is also a longitudinal displacement of second mouth part 10' which is oriented distally, that is to say parallel to the longitudinal axis of first mouth part 10 in the direction of its tip 16. Conversely, during a closing movement of mouth parts 10, 10', there is longitudinal displacement of second mouth part 10' in the proximal direction.

As a result of this, tissue which is located between both mouth parts 10, 10', is ultimately drawn into tool head 30 (see FIG. 2). Furthermore, according to the invention, the lift of second tip 16, that is to say the distance between first and second tip 16, 16', is considerably greater with the same opening angle (cf. FIG. 9, right-hand side). In one embodiment, the length of mouth parts 10, 10' in relation to the distance of the longitudinal axis of first mouth part 10 to the fulcrum is in the ratio of approx. 10:1.

Figure 3:
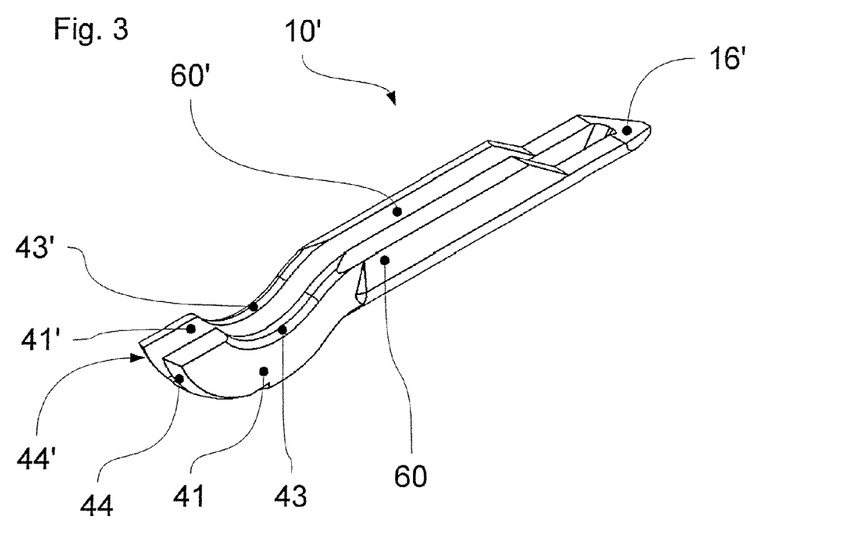
FIG. 3 illustrates the second mouth part in a perspective lateral view according to a disclosed embodiment.
Figure 4:
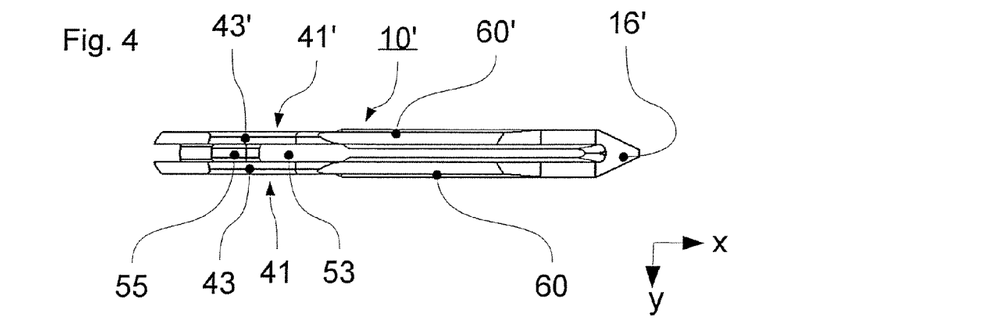
FIG. 4 illustrates the second mouth part in a view from above according to a disclosed embodiment.

Whilst in FIG. 9 relocated fulcrum 1 is achieved, for the sake of clarification, by way of extensions attached vertically on the proximal ends of mouth parts 10, 10', in a preferred embodiment the formation of fulcrum 1 is purely virtual. This virtual design is achieved by a slotted guide system as is explained below on the basis of FIGS. 3-8. Thus, as shown in FIG. 3, second mouth part 10' has two curved articulation guide rails 41, 41' on its proximal end opposing tip 16'. Seen from above (c. FIG. 4), these articulation guide rails 41, 41' run substantially parallel along the longitudinal axis of second mouth part 10' and are spaced apart to form a channel.

Seen from the side (cf. FIG. 5), second mouth part 10' has a spoon-shaped profile. The proximal end of second mouth part 10', in particular articulation guide rails 41, 41', thus each have on their upper side a concave section 43, 43', which engages with first mouth part 10. As can be seen from FIG. 6, to achieve this mouth part 10 has two articulation guide pins 42, 42', each of which has a convex structural section. During the opening and closing movement of mouth parts 10, 10', concave section 43 of first articulation guide rail 41 slides over the adjacent, convex section of first articulation guide pin 42 and concave section 43' of second articulation guide rail 41' slides over the adjacent, convex section of second articulation guide pin 42'. The curvature of concave sections 43, 43' of both articulation guide rails 41, 41' and the corresponding sections of articulation guide pins 42, 42' are determining for the position of virtual fulcrum 1. With a more pronounced curvature, fulcrum 1 lies closer to tool head 30 than with a less pronounced curvature. The effects described in respect of FIG. 9 occur correspondingly more or less pronounced.

Compared to articulations that only have a single-point connection, the guide mechanisms or articulation 40 additionally have the advantage of high stability. Due to the convex and concave sections which engage with each other, a large-area contact region is formed and articulation 40 can absorb significantly more force than an articulation with a single-point connection. To further stabilize articulation 40, first mouth part 10 (see FIGS. 6-8) comprises a first articulation guide bearing 46 and a second articulation guide bearing 46'. Like articulation guide pins 42, 42', articulation bearings 46, 46' are attached alternately on the inside of the sidewalls of first mouth part 10.

First articulation guide bearing 46 and first guide pin 42 are spaced apart such that they accommodate first articulation guide rail 41 in the space between them. First articulation guide bearing 46 has a concave cross-section, which engages with convex section 44 of first articulation guide rail 41. On opening and closing tool head 30, first articulation guide rail 41, guided by first guide pin 42 and first articulation guide bearing 46, rotates about fulcrum 1 (see FIG. 5).

Figure 5:
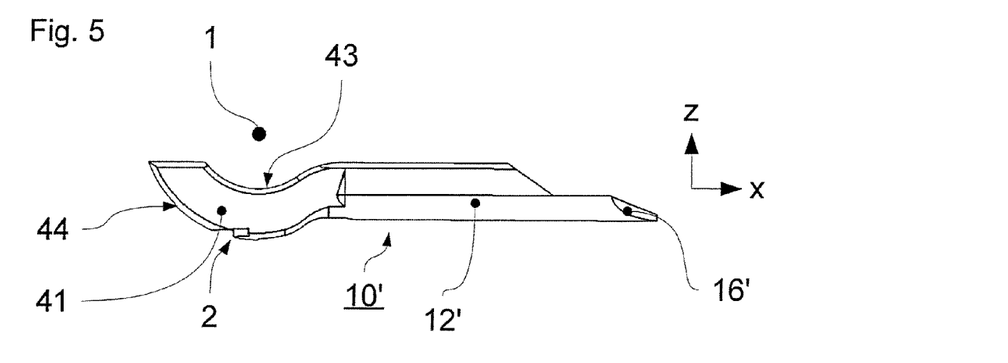
FIG. 5 illustrates the second mouth part in a lateral view according to a disclosed embodiment.
Figure 6:
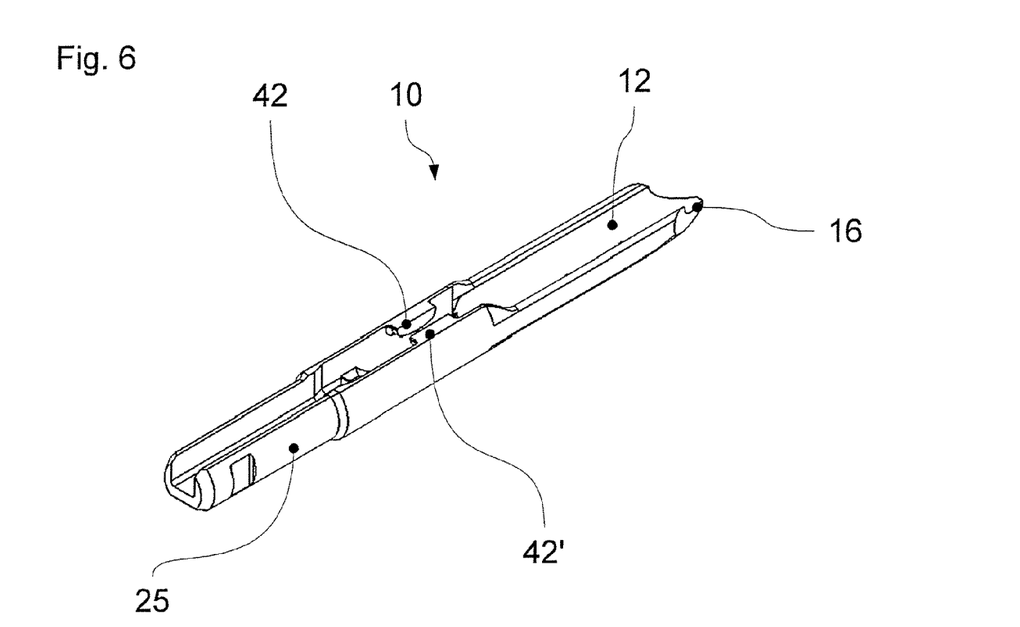
FIG. 6 illustrates the first mouth part in a perspective lateral view according to a disclosed embodiment.
Figure 7:
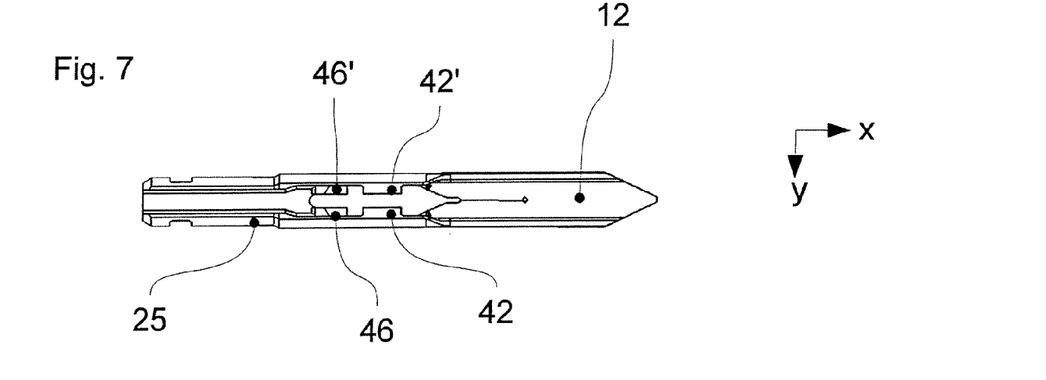
FIG. 7 illustrates the first mouth part in a view from above according to a disclosed embodiment.
Figure 8:
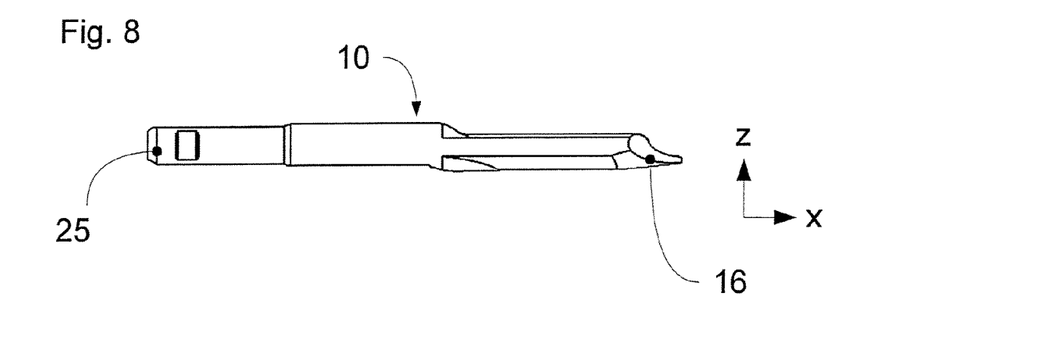
FIG. 8 illustrates the first mouth part in a lateral view according to a disclosed embodiment.

Likewise, second articulation guide rail 41', guided by second guide pin 42' and articulation guide bearing 46', rotates about fulcrum 1 (see FIG. 5). For this, second articulation guide rail 41', second articulation guide pin 42', a convex section 44' of second articulation guide rail 41' and second articulation guide bearing 46' are designed and disposed symmetrically to first articulation guide rail 41, first articulation guide pin 42, convex section 44 of first articulation guide rail 41 and first articulation guide bearing 46.

Figure 10:
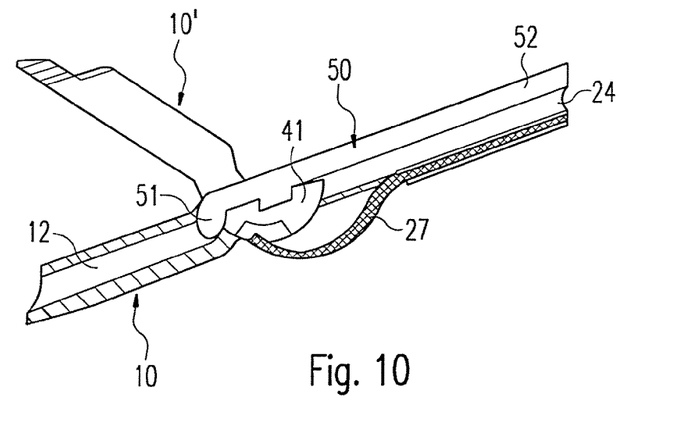
FIG. 10 illustrates a cross-section through the tool head from FIG. 2 with a cutting device according to a disclosed embodiment.
Figure 19:
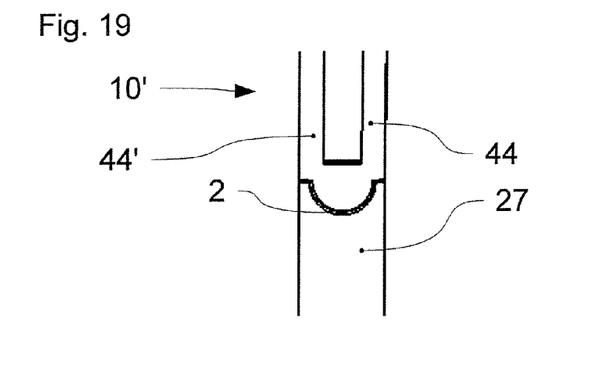
FIG. 19 illustrates the second mouth part with tension strip according to a disclosed embodiment.

As shown in FIG. 10, a tension strip 27 is attached on the proximal end of second mouth part 10'. More precisely, it is attached approximately centrally on convex sections 44, 44' of articulation guide rails 41, 41'. To achieve this, articulation guide rails 41, 41' have a profile for forming an abutting edge 2 (FIG. 5). Preferably, this abutting edge 2 does not run in a straight line parallel to fulcrum 1 but is designed in a semi-circular shape (cf. FIG. 19). Due to this elongated abutting edge 2, along which second mouth part 10' and tension strip 27 are welded, the transmission of force into tension strip 27 is homogenised and the tensile and flexural loading capacity of the weld is significantly increased. In alternative embodiments, acute-angled welds or welds with multiple serrations, which provide a comparable result, are conceivable. Tension strip 27 is substantially wider than it is thick parallel to fulcrum 1. This ensures resilience and bendability of tension strip 27 on rotation of second mouth part 10'. In the longitudinal direction of the tubular shaft instrument, however, tension strip 27 is relatively stiff such that shear forces may also be generated.

By attaching a first end of tension strip 27 to convex sections 44, 44' of articulation guide rails 41, 41', it is ensured that the tensile force exerted by means of tension strip 27 always acts substantially tangentially to the circular motion of curved articulation guide rails 41, 41' about fulcrum 1. Thus a uniform transmission of force independent of the opening angle is assured. A second end of tension strip 27 is operatively connected to handle 110 and may be displaced by means of a control device provided thereon. Due to virtual fulcrum 1, which, as already explained, is located outside and above mouth parts 10, 10', the distance between fulcrum 1 and the first end of tension strip 27 is significantly greater than the distance achieved with normal articulations. Thus the embodiment of the tubular shaft instrument described has a significantly higher leverage by means of which second mouth part 10' may be moved over tension strip 27.

Both mouth parts 10, 10' each have a clamping surface 12, 12' for fixing the tissue. First mouth part 10 thus has, on a distal section, a first clamping surface 12 which faces upwards. First clamping surface 12 is formed substantially concave transverse to the longitudinal axis of first mouth part 10. In the closed state of tool head 30, convex second clamping surface 12' of second mouth part 10' lies substantially parallel to this first clamping surface 12.

In the embodiment described, these clamping surfaces 12, 12' are not only suitable for securely fixing the tissue to be cut later, they also form the electrodes for a coagulation process. To achieve this, sections of clamping surfaces 12, 12' are electrically conductive and connected via printed conductors to a high-frequency current source, which is also controllable by way of handle 110. Thus the tissue gripped may be cauterised to such an extent prior to the cutting procedure that separation is possible without bleeding. Preferably, sections at least of mouth parts 10, 10' are manufactured from ceramic material by the injection moulding method. Thus the guide elements, in particular articulation guide rails 41, 41' and articulation guide pins 42, 42' of articulation 40, are easy to form. Articulation 40 of ceramic material forms an electrical insulation between mouth parts 10, 10', in particular between their electrodes for coagulation.

Figure 11:
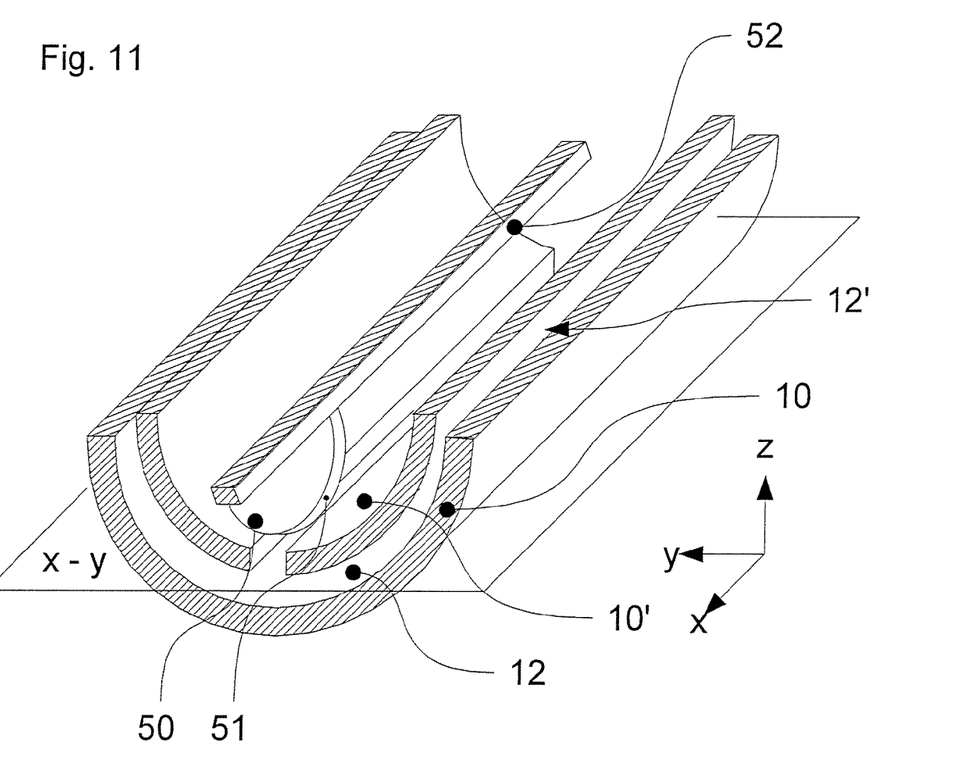
FIG. 11 illustrates a schematic diagram of the cutting device according to a disclosed embodiment.

In the present embodiment, the actual mechanical cutting process takes place after coagulation. To achieve this, a cutting device 50 is moved parallel to a fixing plane x-y (cf. FIG. 11), which is defined by clamping surfaces 12, 12'. This cutting device 50 comprises a blade 51 for separating the tissue in addition to a guide wire 52 by means of which a displacement of blade 51 in the longitudinal direction of the tubular shaft instrument (x-axis) is possible.

Prior to the cutting process, blade 51 is drawn back so far towards tubular shaft 24 that premature injury of the tissue is not possible. Preferably, the blade in first mouth part 10 is at the level of articulation guide pins 42, 42'. From this starting position, blade 51 is brought onto fixing plane x-y by way of a ramp 55 integrated in second mouth part 10' (cf. FIG. 4 for this). This ramp 55 is located between the two articulation guide rails 41, 41'. Second mouth part 10' provides a blade guide 53 for the displacement of blade 51 or the cutter. This blade guide 53 is an oblong opening extending along the longitudinal axis of second mouth part 10'. In order to hold blade 51 perpendicular to fixing plane x-y, second mouth part 10' has in its central region side parts 60, 60', which are disposed parallel to each other in such a way that they form a channel extending lengthways. Blade 51 or the cutter is guided in this channel.

Figure 12:
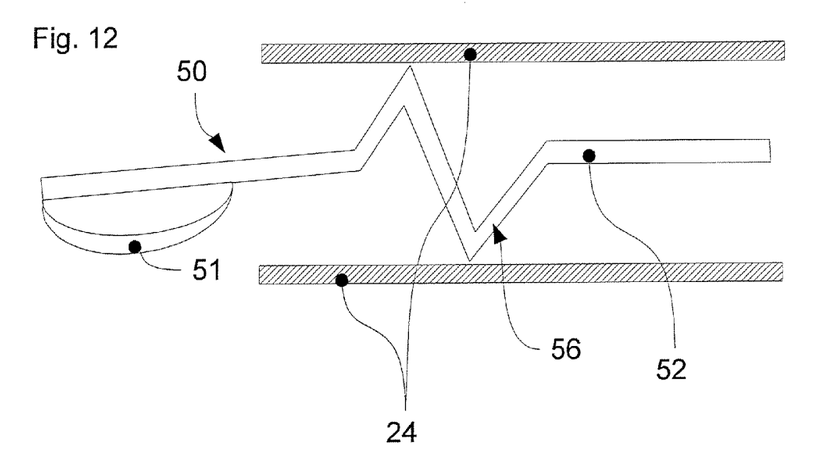
FIG. 12 illustrates a schematic view of the cutting device in a tubular shaft of a tubular shaft instrument according to a disclosed embodiment.

After closing mouth parts 10, 10', blade 51 thus glides out of its starting position over ramp 55 into said channel and may there be pulled or pushed distally and proximally over the tissue. Blade 51 is preloaded in relation to fixing plane x-y in order to ensure that this displacement separates the tissue step by step. A preloading device exerts a force perpendicular to fixing plane x-y, which presses blade 51 against the plane. This force is built up via the resilience of guide wire 52 and its curvature. As can be seen from FIG. 12 guide wire 52 is curved perpendicular to fixing plane x-y in the plane preloaded by blade 51. A crimp 56 is located in a front section of guide wire 52. Crimp 56 is integrated in guide wire 52 in such a manner that in the fully extended state of cutting device 50, that is to say when blade 51 is at the distal end of mouth parts 10, 10', the crimp in tubular shaft 24 is likewise at the distal end of said shaft. Crimp 56 is used to transfer at least part of the force exerted by the curvature of guide wire 52 perpendicular to fixing plane x-y to tubular shaft 24 and has corresponding contact points. The curvature of guide wire 52 is provided such that if the proximal end of the guide wire runs parallel to tubular shaft 24, the distal end of unattached guide wire 52 is curved downwards and blade 51 lies at least partially below fixing level x-y. Guide wire 52 is operatively connected to handle 110 in such a manner that blade 51 can be moved back and forth in tool handle 30 by means thereof.

The most varied embodiments are conceivable in respect of the design of blade 51. These will be described in the following on the basis of FIGS. 13, 14 and 15. One idea of the invention is that blade 52 has at least one section which runs substantially parallel to fixing plane x-y and thus parallel to the fixed tissue. Consequently, during the cutting procedure blade 51 glides over the tissue until it is completely separated. Unlike in conventional cutting procedures, it can thus be ensured that even when blade 51 is blunt the tissue will be separated and will not be crushed due to the mechanical pressure. The section of the cutting blade formed parallel to fixing plane x-y likewise has the advantage that blade 51 rests on the tissue not only at a point but usually over a longer region. Therefore wearing of blade 51 at certain points is prevented.

Figure 13:
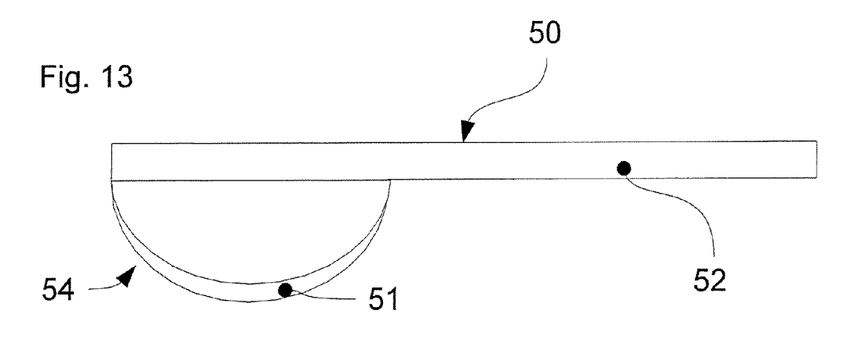
FIG. 13-15 illustrate three embodiments of a cutting blade according to a disclosed embodiment.

FIG. 13 shows a semicircular blade 51, having a convex curvature. Blade 51 is disposed on the underside of guide wire 52. It has a blade curvature 54 distal and proximal to the tubular shaft instrument.

Figure 14:
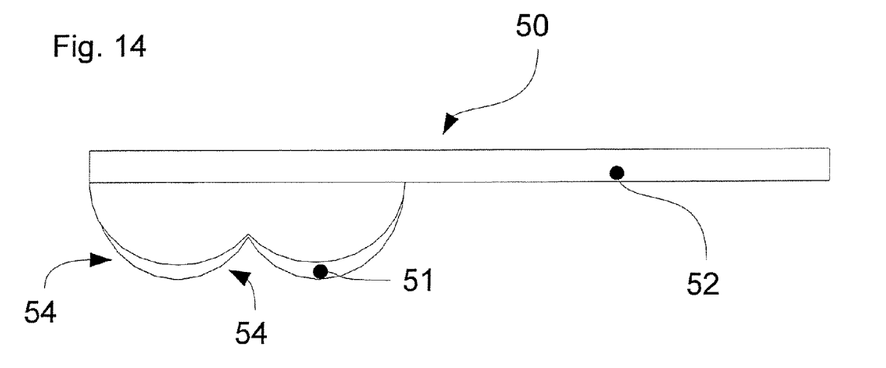

FIG. 14 shows a blade 51, comprising two semicircles each disposed one behind the other.

Figure 15:
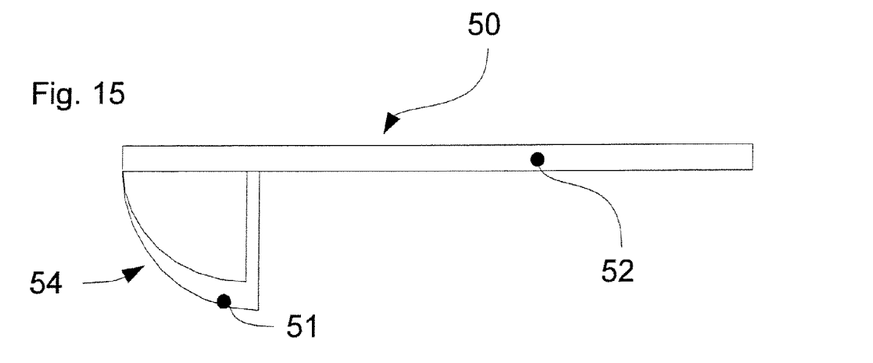

FIG. 15 shows a blade 51, having a blade curvature 54 distally, and a section perpendicular to guide wire 52 proximally.

Preferably, blade 51 is microtoothed overall.

In an alternative embodiment (cf. FIG. 10 for example), guide wire 52 is a rail. The rail may be designed in such a manner that it has the same functionality as guide wire 52. Preloading in relation to fixing plane x-y may be achieved by means of the rails intrinsic resilience or by means of a separate device (e.g. a spring).

The advantageous cutting device 50 of the invention has been described so far in conjunction with the advantageous articulation shape. Both inventions, however, may also be executed separately from one another.

Figure 17:
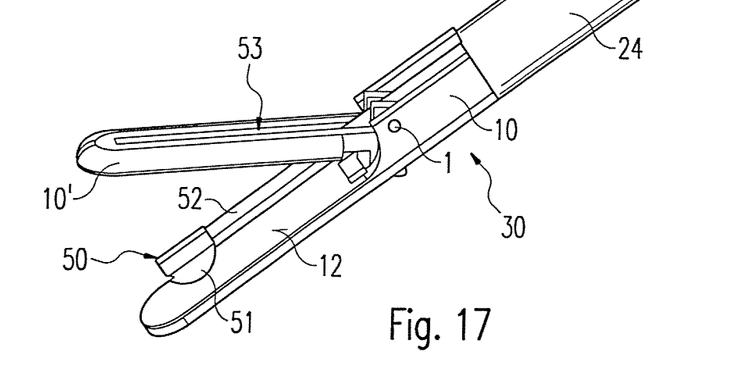
FIG. 17 illustrates a perspective view of a tool head in an open position according to a disclosed embodiment.
Figure 18:
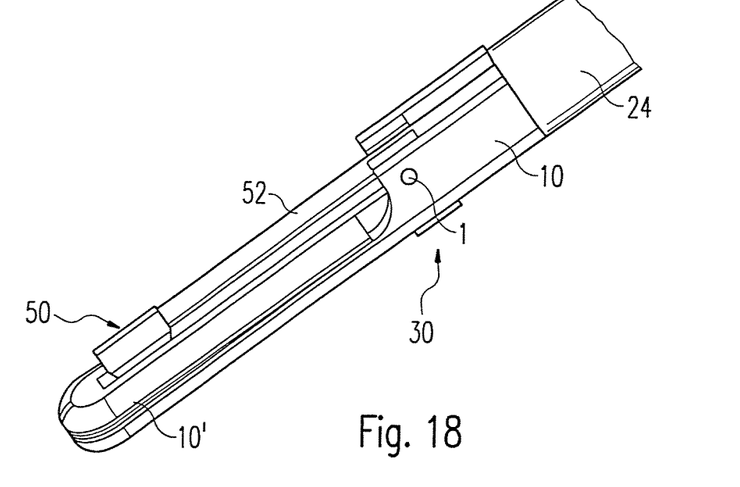
FIG. 18 illustrates the tool head from FIG. 17 in a closed position according to a disclosed embodiment.

Thus, FIGS. 17 and 18, for example, show cutting device 50 in a tool head 30, whereby second mouth part 10' is not in operative connection with first mouth part 10 by way of a slotted guide system. Here fulcrum 1 lies substantially on the longitudinal axis of mouth parts 10, 10'.

Figure 16:
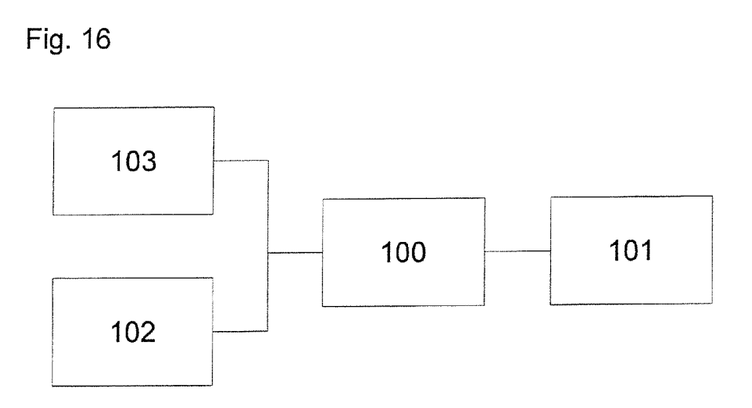
FIG. 16 illustrates a block diagram of an incision monitoring device according to a disclosed embodiment.

In one embodiment according to the invention, the tubular shaft instrument further comprises a cut monitoring device. This determines when the tissue between the two clamping surfaces 12, 12' is completely separated. In the embodiment, blade 51 rests on first clamping surface 12 when the tissue is completely separated. As clamping surface 12 comprises an electrode for coagulation, it is electrically conductive in parts at least. According to the invention, at least one section of blade 51, which mechanically contacts separating surface 12 when the tissue is separated, is likewise formed of electrically conductive material. The electrical contact between blade 51 and clamping surface 12 is determined by means of a cut monitoring device. The gripped tissue is deemed to be completely separated when a continuous electrical contact exists between blade 51 and clamping surface 12 during a complete cutting movement by tip 16' of second mouth part 10' up to ramp 55. As can be seen from FIG. 16, the cut monitoring device comprises a processing unit 100, a display device 101, a switch 103 and a travel sensor 102 for determining and displaying the progress of the cutting procedure. Travel sensor 102 determines the position or displacement of blade 51 and consequently helps to define an observation period that preferably covers a complete blade movement. Switch 103 is formed in the simplest case by means of electrically conductive blade 51 and first clamping surface 12. As the tissue to be cut has a certain electrical conductivity, electric switch 103 is only deemed to be closed when a low-ohm connection exists between clamping surface 12 and blade 51. A corresponding device is connected upstream of processing unit 100. If processing unit 100 ascertains that there is a continuous low-ohm contact between blade 51 and clamping surface 12 during a complete observation period, it indicates to the user by means of display device 101 that the gripped tissue has been separated completely. Therefore cutting device 50 is treated with care since the displacement of blade 51 over clamping surface 12 without tissue sandwiched between damages the device.

Alternatively, it may also be constantly indicated to the user whether there is a direct mechanical contact between blade 51 and clamping surface 12. As the user performs the movement of blade 51 manually, he can draw conclusions independently as to whether the tissue is adequately separated.

In a further embodiment, travel sensor 102 comprises two electrical contact regions on the distal and proximal end of blade guide 53, which are designed in such a manner that it is possible to determine contacting between blade 51 and the distal contact region as well as between blade 51 and the proximal contact region. Processing unit 100 can thus determine the start and end of the observation interval.

Figure 20:
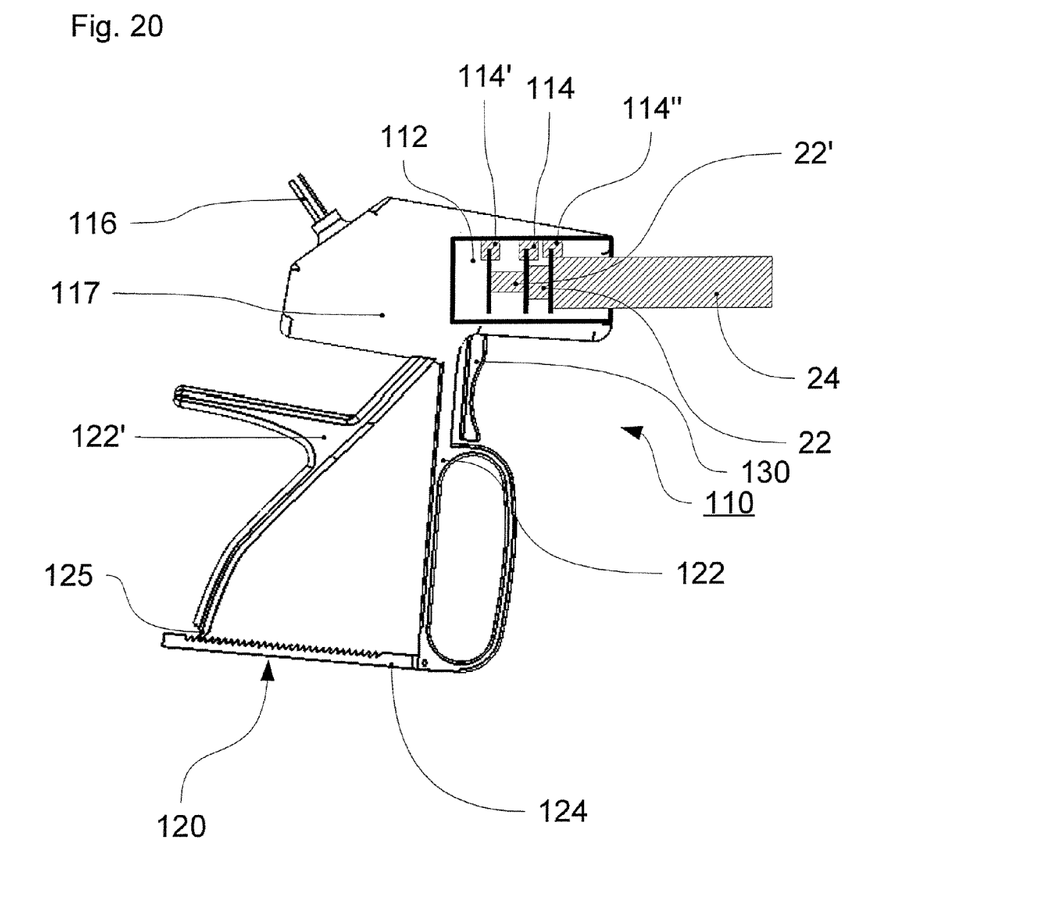
FIG. 20 illustrates a schematic lateral view of the tubular shaft instrument according to a disclosed embodiment.

FIG. 20 shows a schematic detail view of handle 110 from FIG. 1. Handle 110 comprises a handle body 117 on the underside of which a first handle lever 122 is integrally formed. This handle lever 122 has an opening for receiving a plurality of fingers, preferably the middle, ring and little finger. A second handle lever 122' is rotatably joined to handle body 117 close to first handle lever 122. Mouth parts 10, 10' of tool head 30 may be opened and closed by means of a displacement of second handle lever 122' relative to first handle lever 122 proximally and distally. Handle levers 122, 122' form a hand trigger 120 and can thus be grasped in the user's hand such that the entire tubular shaft instrument can be guided with one hand. To achieve this, the hand encloses sections of handle lever 122, 122'. Located on the end of second handle lever 122' facing away from handle body 117 is an extension which engages in a toothed rack 124. This toothed rack 124 is attached at a right angle to the longitudinal axis of first handle lever 122 on its end facing away from handle body 117. The toothing of toothed rack 124 is designed in such a manner that second handle lever 122' can be moved step by step towards handle lever 122 and the position correspondingly set remains without the continued exertion of a force. In order to release this fastening of handle levers 122, 122' to each other, toothed rack 124 is pressed away from extension 125 in such a manner that they are no longer engaged.

Moreover, handle 10 has a finger trigger 130, which is likewise rotatably attached to handle body 117. Cutting device 50, in particular blade 51, may be displaced distally by operating finger trigger 130. A spring element (not illustrated) inside handle body 117 returns finger trigger 130 to its starting position after operation, as a result of which cutting device 50 is displaced proximally. Finger trigger 130 is disposed distally in front of first handle lever 122 in such a manner that finger trigger 130 can be operated with the first finger on grasping handle levers 122, 122'.

Handle 10 has a momentary contact switch 116 on the proximal side of handle body 117, which controls the coagulation current. In an alternative embodiment, it is possible in place of momentary contact switch 116 to provide a control device having a plurality of actuating elements by means of which a plurality of coagulation modes may be selected and performed. It is likewise conceivable to provide display device 101 on handle body 117.

In one embodiment according to the invention, tubular shaft 24 and handle 110 are designed in such a manner that tubular shaft 24 may be detachably inserted into handle 110. To achieve this, a receiving opening 112, which can be closed by means of a cover, is located on the side of handle 110.

Thus, prior to the operation, a sterile disposable tubular shaft 24 having appropriate tool head 30 and cutting device 50 is inserted into reusable handle 110 and locked therein. Reuse of tubular shaft 24 and the associated devices is not envisaged. Handle body 117 has a first coupling element 114 or a coupling element, a second coupling element 114' or a coupling element and a third coupling element 114" or a coupling element for mechanical connection of tool head 30, cutting device 51 and tubular shaft 24. A ring provided on the proximal end of tubular shaft 24 engages with third coupling element 114" in such a manner that the tubular shaft is rigidly connected to handle body 117. A first inner tube adapter 22 engages, by means of a ring likewise disposed on the proximal end, with first coupling element 114, which is in operative connection with second handle lever 122'. The displacement of second handle lever 122' is transferred to first coupling element 114 by means of a mechanism disposed inside handle body 117 and transfers this displacement in turn to first inner tube adapter 22. This is directly or indirectly joined mechanically to second mouth part 10' by way of tension strip 27. A longitudinal displacement of first inner tube adapter 22 in relation to tubular shaft 24 thus brings about opening and closing of mouth parts 10, 10'.

A second inner tube adapter 22' is disposed movably in relation to first inner tube adapter 22 inside said first inner tube. This inner tube adapter 22' is operatively connected to guide wire 52 and displaces blade 51. Inserting tubular shaft 24 into handle body 117 engages a proximal ring on the end of second inner tube adapter 22' with second coupling element 114' and transfers the displacement or the force exerted by means of finger trigger 130 to cutting device 50.

In order to make it easier to insert disposable tubular shaft 24, a removable fastening is provided thereon, which holds inner tube adapter 22, 22' in a predetermined position relative to tubular shaft 24, which is designed in such a manner that the rings are easily insertable into coupling elements 114, 114', 114".

Coupling elements 114, 114', 114" are designed in such a manner that tubular shaft 24 may be rotated in relation to handle 110. Thus the alignment of tool head 30 can be adjusted freely in relation to handle 110. During rotation, the rings of inner tube adapters 22, 22' and of tubular shaft 24 rotate in coupling elements 114, 114', 114" and thus form an articulation.

LIST OF REFERENCE NUMBERS

1 Fulcrum
2 Abutting edge
10, 10' Mouth part
12, 12' Clamping surface
16, 16' Tip
20 Tubular shaft instrument
22, 22' Inner tube adapter
24 Tubular shaft
25 Adapter
27 Tension strip
30 Tool head
40 Articulation
41, 41' Articulation guide rail
42, 42' Articulation guide pin
43, 43' Concave section of the articulation guide rail
44, 44' Convex section of the articulation guide rail
46, 46' Articulation guide bearing
50 Cutting device
51 Blade
52 Guide wire
53 Blade guide
54 Blade curvature
55 Ramp
56 Crimp
60, 60' Side part
100 Processing unit
101 Display device
102 Travel sensor
103 Switch
110 Handle
112 Receiving opening
114, 114', 1144" Coupling element
116 Momentary contact switch
117 Handle body
120 Hand trigger
122, 122' Handle lever 124 Toothed rack
125 Extension
130 Finger trigger
x x-axis
y y-axis
z z-axis

The invention claimed is:

1. A tubular shaft instrument for separating tissue, comprising:
a tubular shaft;
a first and a second mouth part each having at least one clamping surface for fixing tissue in a fixing plane which extends along a longitudinal axis of the instrument, whereby at least one of the mouth parts is joined to the tubular shaft; and
a cutting device having a blade that is for cutting of the fixed tissue and that is displaceable in a cutting direction by means of an actuating device,
wherein at least one of the mouth parts comprises an opening extending along the cutting direction, which forms a blade guide for guiding the blade during cutting,
wherein the blade is displaceably guided substantially parallel to the fixing plane and is preloaded with a force that is perpendicular to the fixing plane during cutting by means of a preloading device, and
wherein the blade is curved such that the blade glides over the tissue preloaded in the fixing plane when moved back and forth within the blade guide.

2. The tubular shaft instrument according to claim 1, wherein the preloading device comprises a resilient guide wire having a curvature, whereby the guide wire is substantially rigidly joined to the blade and is guided in the tubular shaft in such a manner that the blade is preloaded in relation to the tubular shaft in the direction of the fixing plane.

3. The tubular shaft instrument according to claim 2, wherein the preloading device includes a crimp which is disposed in the guide wire such that it is close to the distal end of the tubular shaft when the blade is pushed forward.

4. The tubular shaft instrument according to claim 1, wherein the blade comprises at least one section, which runs substantially parallel to the fixing plane.

5. The tubular shaft instrument according to claim 1, wherein the blade is curved so as to be convex in sections at least.

6. The tubular shaft instrument according to claim 1, further comprising a ramp-shaped blade guide disposed such that, by moving the blade in the direction of cutting, the blade guide brings the blade out of a starting position at a distance from the fixing plane onto the fixing plane.

7. The tubular shaft instrument according to claim 6, wherein the mouth parts are disposed rotatably to one another and the blade guide is configured such that the blade may be brought into a starting position close to a fulcrum of the mouth parts.

8. The tubular shaft instrument according to claim 1, wherein the clamping surfaces comprise electrodes for supplying high-frequency coagulation currents to the gripped tissue.

9. The tubular shaft instrument according to claim 1, wherein the blade is microtoothed at least in sections.

10. The tubular shaft instrument according to claim 1, further comprising at least one articulation for rotatably supporting the mouth parts in such a manner that the mouth parts may be brought from an open position into a closed position in order to fix the tissue using the clamping surfaces, whereby the articulation is designed in such a manner that a fulcrum of the articulation is located outside the mouth parts and the distal end of at least one mouth part is displaceable away from the distal end of the tubular shaft on opening.

11. The tubular shaft instrument according to claim 10, wherein the at least one articulation includes a slotted guide system.

12. The tubular shaft instrument according to claim 10, wherein the at least one articulation comprises an articulation guide on one of the two mouth parts and at least one rail or groove on the other of the two mouth parts.

13. The tubular shaft instrument according to claim 10, wherein the at least one articulation comprises at least two partial articulations which are spaced apart from one another to form a passage disposed centrally between said partial articulations.

14. The tubular shaft instrument according to claim 1, wherein one of the two mouth parts is rigidly connected to the tubular shaft.

15. The tubular shaft instrument according to claim 1, further comprising a strip that is displaced substantially linearly when used for opening and closing of one of the mouth parts to be displaced, said strip being attached by means of a resilient end section on the mouth part to be displaced.

16. The tubular shaft instrument according to claim 15, wherein the strip is a tension strip, the end section of which is permanently attached to the mouth part to be displaced.

17. The tubular shaft instrument according to claim 16, wherein the strip is attached to the mouth part by means of welding.

18. The tubular shaft instrument according to claim 10, wherein at least one of the mouth parts comprises, at least in the region of the at least one articulation, an electrically insulating material.

19. The tubular shaft instrument according to claim 1, further comprising a removable handle, comprising:
a first and a second mechanical actuating element;
a first force transmission element for removable coupling of the first actuating element to a first functional unit; and
a second force transmission element for removable coupling of the second actuating element to a second functional unit.

20. The tubular shaft instrument according to claim 19, wherein the tubular shaft and the mouth parts are a disposable unit and are replaceably joined to the handle by way of the force transmission elements.

21. The tubular shaft instrument according to claim 20, wherein the disposable unit is pre-positioned prior to installation in the handle by means of a fastening in such a manner that the force transmission elements may be engaged with corresponding matching parts when installed.

22. The tubular shaft instrument according to claim 1, wherein the tubular shaft instrument is an electrosurgical tubular shaft instrument.

23. The tubular shaft instrument according to claim 16, wherein the strip is comprised of spring steel.

24. The tubular shaft instrument according to claim 17, wherein the strip is attached to the mouth part via a weld joint that is square in relation to a longitudinal axis of the strip.

25. The tubular shaft instrument according to claim 17, wherein the strip is attached to the mouth part via a weld joint that is curved in relation to a longitudinal axis of the strip.

26. The tubular shaft instrument according to claim 18, wherein the electrically insulating material is a ceramic material.

27. The tubular shaft instrument according to claim 19, wherein the first functional unit is at least one of the mouth parts of the tool head, and the second functional unit is a cutting device of the tool head.

28. A tubular shaft instrument for separating tissue, comprising:
- a tubular shaft;
- a first and second mouth part each having at least one clamping surface for fixing tissue in a fixing plane, whereby at least one of the mouth parts is joined to the tubular shaft; and
- a cutting device having a blade that is for cutting of the fixed tissue and that is displaceable in a cutting direction by means of an actuation device,
- wherein the blade is displaceably guided substantially parallel to the fixing plane and is preloaded against the fixing plane during cutting by means of a preloading device,
- wherein the preloading device comprises a resilient guide wire having a curvature or a resilient guide rail, whereby the guide wire/rail is substantially rigidly joined to the blade and is guided in the tubular shaft in such a manner that the blade is preloaded in relation to the tubular shaft in the direction of the fixing plane.

\* \* \* \* \*